United States Patent [19]

Nösberger

[11] Patent Number: 5,214,162
[45] Date of Patent: May 25, 1993

[54] PROCESS FOR MANUFACTURING 5-CYANO-4-LOWER ALKYLOXAZOLES

[75] Inventor: Paul Nösberger, Birsfelden, Switzerland

[73] Assignee: Hoffman-La Roche Inc., Nutley, N.J.

[21] Appl. No.: 803,004

[22] Filed: Dec. 5, 1991

[30] Foreign Application Priority Data

Dec. 21, 1990 [CH] Switzerland ............ 4075/90

[51] Int. Cl.$^5$ ............................................. C07D 263/34
[52] U.S. Cl. ................................................... 548/236
[58] Field of Search .................... 548/236; 558/311

[56] References Cited

U.S. PATENT DOCUMENTS

| | | | |
|---|---|---|---|
| 2,901,504 | 8/1959 | Aries | 558/311 |
| 3,222,374 | 12/1965 | Chase | 260/307 |
| 4,011,234 | 3/1977 | Hoffman-Paquotte | 260/307 R |
| 4,026,901 | 5/1977 | Coffen | 260/307 R |
| 4,093,654 | 6/1978 | Coffen | 260/561 A |
| 4,255,584 | 3/1981 | Hoffmann-Paquotte | 548/236 |
| 4,772,718 | 9/1988 | Nosberger | 548/236 |

OTHER PUBLICATIONS

Stepanova et al., *Chem. Abstracts*, 85:519 No. 143020x (1976).

*Primary Examiner*—Patricia L. Morris
*Attorney, Agent, or Firm*—George M. Gould; William H. Epstein; Catherine R. Roseman

[57] ABSTRACT

The invention is concerned with a process for the manufacture of 5-cyano-4-lower alkyl-oxazoles by dehydrating a 5-carbamoyl-4-lower alkyl-oxazole in the gas phase in the presence of a heterogeneous catalyst based on silicon dioxide and in the presence of an inert solvent. The heterogeneous catalyst used is formed $SiO_2$ or $SiO_2$ doped with an oxide of V, Mo, Fe, Co and/or Zn. An N-lower alkyl-pyrrolidone is preferably used as the inert solvent.

10 Claims, No Drawings

PROCESS FOR MANUFACTURING 5-CYANO-4-LOWER ALKYLOXAZOLES

SUMMARY OF THE INVENTION

The invention is concerned with a process for the manufacture of 5-cyano-4-lower alkyl-oxazoles, especially 5-cyano-4-ethyl-oxazole and 5-cyano-4-methyl-oxazole. These are compounds of the formula:

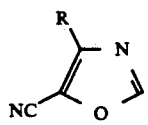
  I where R is lower alkyl.

These oxazoles form an important group of substances. For example, 5-cyano-4-methyl-oxazole is a valuable intermediate in the synthesis of pyridoxine (vitamin $B_6$).

BACKGROUND OF THE INVENTION

Several processes for the manufacture of 5-cyano-4-lower alkyl-oxazoles have already been described. The synthesis of 5-cyano-4-methyl-oxazole is carried out, for example, by dehydrating 5-carbamoyl-4-methyl-oxazole in the presence of phosphorus pentoxide. The disadvantage of this process is the low yield of product due to carbonization, which occurs very readily in this reaction.

An improvement of this process comprises reacting 5-carbamoyl-4-methyl-oxazole with phosphorus pentoxide in the presence of quinoline as the solvent (U.S. Pat. No. 3,222,374). This process also has disadvantages which result mainly from the use of quinoline, which is toxic, has an unpleasant smell, and is thermally unstable. Also, quinoline is a relatively expensive solvent. A further problem is the regeneration of quinoline. Phosphorus pentoxide also presents problems. It must be used in stoichiometric amounts and its by-products must be worked up and disposed of in an environmentally correct manner.

Another known process (U.S. Pat. No. 4,011,234) for the manufacture of 5-cyano-4-methyl-oxazole comprises reacting 5-carbamoyl-4-methyl-oxazole with a lower alkanecarboxylic acid anhydride and subjecting the reaction mixture or the 4-methyl-5-(N-lower alkanoyl-carbamoyl)-oxazole isolated therefrom to a pyrolysis. However, the final pyrolytic step has certain disadvantages. In particular, corrosion problems with the reactor materials occur and byproducts which are difficult to recycle are formed.

The one-step conversion of 5-ethoxycarbonyl-4-methyl-oxazole into 5-cyano-4-methyl-oxazole is disclosed in U.S. Pat. No. 4,772,718. In this process the oxazole ester is converted into the cyano-oxazole in the presence of ammonia and a zirconium oxide or hafnium oxide catalyst in the gas phase. Disadvantages are the use of the relatively expensive catalyst, and the maintenance of very precise reaction conditions in order to optimize reaction control.

A further process (U.S. Pat. No. 4,026,901) comprises catalytically dehydrating 5-carbamoyl-4-methyl-oxazole to 5-cyano-4-methyl-oxazole while heating in the presence of phosphorus pentoxide on a solid carrier. Handling 5-carbamoyl-4-methyl-oxazole is a disadvantage of this process. Sublimation is a prime consideration, and so is the solid dosing of the low volatility starting material.

The subject invention is a process for the manufacture of 5-cyano-4-lower alkyl-oxazoles which does not have the disadvantages of the state of the art.

DETAILED DESCRIPTION OF THE INVENTION

The object of the invention is accordingly a process for the manufacture of 5-cyano-4-lower alkyl-oxazoles by the catalytic dehydration of a 5-carbamoyl-4-lower alkyl-oxazole in the gas phase. The 5-carbamoyl-4-lower alkyl-oxazole is used in the presence of an inert solvent, evaporated as the solution, fed into a reactor, and catalyzed with a catalyst base on silicon dioxide, according to the following reaction scheme:

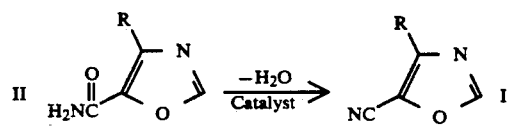

where R is lower alkyl.

The 5-carbamoyl-4-lower alkyl oxazole of formula II is converted to the 5-cyano-4-lower alkyl oxazole of formula I by contacting formula II while in a gaseous state with a silicon dioxide catalyst, converting it into formula I. Formula II is obtained in its gaseous phase by dissolving or suspending it in an inert solvent which has a boiling point preferably higher than the melting point of formula II, and heating the resulting solution or suspension to evaporation.

An example of a lower alkyl group is an alkyl group having from 1 to 6 carbon atoms and which is straight-chain or branched. The alkyl group is preferably straight-chain $C_{1-3}$-alkyl, especially methyl or ethyl.

Formed silicon dioxide (spheres, tablets, pressings etc.) can be used as the catalyst. The silicon dioxide can be coated with oxides of V, Mo, Fe, Co and/or Zn in order to increase catalytic activity and selectivity. The coating can be carried out in a known manner, for example by dissolving a water-soluble salt of the desired metal in distilled water, impregnating the silicon dioxide with this solution, drying the impregnated silicon dioxide and calculating it at a sufficiently high temperature (for example about 500° C.).

The catalysts which are used in accordance with the invention are commercially available or can be produced in a manner known per se, such as that described above.

The specific surface area of the non-coated (doped) silicon dioxide catalyst or of the silicon dioxide catalyst doped with oxides of V, Mo, Fe, Co and/or Zn may be in the range of about 20–300 $m^2/g$. The doped catalyst may contain oxides of V, Mo, Fe, Co and/or Zn in an amount of about 1–20 weight percent based on the total weight of the doped catalyst.

Dilution with an inert gas, for example nitrogen (optionally itself diluted with hydrogen), may be employed in order to reduce the deposition of coke which can occur in the reaction. This dilution with an inert gas is optional and is not essential for the performance of the reaction. The reaction is preferably carried out at a pressure of about 50 to about 300 kPa. The reaction pressure may be atmospheric pressure, provided the temperature is such that the 5-carbamoyl-4-lower alkyl-oxazole is converted into a gas.

In general, the contact times of the reactants should be in the range of about 0.1 second to about 10 seconds, with the range of about 0.3 second to about 3 seconds, being especially preferred. The throughput of 5-carbamoyl-4-lower alkyl-oxazole may amount to about 0.1-1.0 kg per liter of catalyst per hour.

The reaction may be effected in a temperature range of about 350° C. to about 500° C., preferably at temperatures between about 400° C. and about 450° C.

In accordance with the invention the 5-carbamoyl-4-lower alkyl-oxazole is introduced into the heated reactor or into the evaporation system in the form of a solution, preferably an almost saturated solution, or as a suspension in an inert solvent, preferably a N-lower alkyl-pyrrolidone. Any undissolved 5-carbamoyl-4-lower alkyl-oxazole will dissolve in the solvent at the boiling point at latest, and is then introduced together with the solvent into the heated reactor zone. The gaseous educt/solvent mixture, optionally diluted with an inert gas, as described, is conducted through the heated reactor zone which is filled with the catalyst. The gaseous products are condensed and separated in the usual manner. The yield of 5-cyano-4-lower alkyl-oxazole normally amounts to about 90-95%.

The solvent used should be selected in order that the 5-carbamoyl-4-lower alkyl-oxazole dissolves therein at its boiling point at the latest. The solvent should be thermally stable and inert under the reaction conditions. It should have a boiling point which is higher than the melting point of the 5-carbamoyl-4-lower alkyl-oxazole, and should be readily separable from the 5-cyano-4-lower alkyl-oxazole. Finally, the solvent should be selected so that no deactivation of the catalyst occurs. Any inert solvent or solvent mixture having the appropriate boiling point may be used in accordance with this invention. N-lower alkyl-pyrrolidones are especially suitable inert solvents. N-methyl-pyrrolidones are ethyl-pyrrolidone, optionally diluted with water, are preferred solvents.

The process in accordance with the invention may be carried out continuously, especially in a solid bed reactor which consists, for example, of one or several columns packed with the catalyst. The diameter and the length of the columns are not critical.

This process has particular advantages compared with the known processes for the manufacture of 5-cyano-4-lower alkyl-oxazoles. First, the 5-carbamoyl-4-lower alkyl-oxazole can be introduced into the heated reactor in solution. Second, any unreacted 5-carbamoyl-4-lower alkyl-oxazole does not crystallize out during the condensation, but remains in solution. Finally, the temperature required for the regeneration of the catalyst is approximately the same as the reaction temperature.

The process in accordance with the invention is illustrated further by the following Examples. These Examples are not intended to limit the invention in any way.

EXAMPLE 1

The reactor consists of a vertically arranged glass tube (length 45 cm, diameter 2.3 cm) which is surrounded by an electrically heated tube oven and which is connected to a condenser. The upper part of the glass tube is filled with 60 ml of ceramic spheres, the middle part is filled with 30 ml of catalyst and the bottom part is filled with 30 ml of ceramic spheres. Various commercially available silicon dioxide catalysts are used as the catalyst (Table 1).

The reaction zone is heated to 425°-450° C. and 30 ml of a 10% solution of 5-carbamoyl-4-methyl-oxazole in N-methyl-pyrrolidone as well as 2 liters of nitrogen gas are conducted hourly into the reactor from above. The reaction products are condensed in the condenser and are analyzed by gas chromatography. The results are compiled in Table I.

TABLE 1

| Silicon dioxide | Specific surface ($m^2/g$) | Reaction Temperature °C. | Yield % |
|---|---|---|---|
| Grace XWP 1000 | 33 | 450 | 94 |
| Grace XWP 500 | 71 | 425 | 93 |
| Shell S980 G | 51 | 450 | 92 |
| BASF D11-11 | 65 | 450 | 83 |
| Akzo Si2-5P | 355 | 425 | 89 |

EXAMPLE 2

A silicon dioxide coated with a metal oxide is used in each case as the catalyst. The coating of the silicon dioxide is effected in a known manner: 100 g of silicon dioxide (BASF D11-11) is impregnated with the solution of a dissociatable water-soluble salt of the desired metal in 100 ml of distilled water (see Table 2). The coated silicon dioxide is dried in a rotary evaporator at a pressure of 2.6 kPa and at a temperature 80° C. Subsequently, the catalyst is calcinated for 3hours at 500° C. (heating up rate: 1° C./min.) in an atmosphere of air. The catalysts listed in Table 2 having a coating of 5% of metal oxide.

A silicon dioxide catalyst coated with a metal oxide is filled into the reactor described in Example 1 in place of the pure silicon dioxide. The reaction zone is hatred to about 375°-425° C. and 30 ml of a 10% solution of 5-carbamoyl-4-methyl-oxazole in N-methyl-pyrrolidone as well as 2l is nitrogen gas are conducted hourly into the reactor from above.

The results obtained are compiled in Table 2.

TABLE 2

| Metal oxide salt | Amount (g/100 g $SiO_2$) | Metal oxide | Reaction temperature °C. | Yield % |
|---|---|---|---|---|
| $NH_4VO_3$ | 6.8 | $V_2O_5$ | 425 | 88 |
| $(NH_4)_6Mo_7O_{24}\cdot 4H_2O$ | 7.3 | $MoO_3$ | 375 | 89 |
| $Fe(NO_3)_3\cdot 3H_2O$ | 26.7 | $Fe_2O_3$ | 400 | 95 |
| $Co(NO_3)_2\cdot 6H_2O$ | 20.5 | $CoO$ | 425 | 91 |
| $Zn(NO_3)_2\cdot 6H_2O$ | 19.2 | $ZnO$ | 400 | 94 |

EXAMPLE 3

The reactor consists of two vertically arranged steel tubes (length 70 cm, diameter 2.7 cm) which are connected in series and which are externally heatable. The upper steel tube is filled completely with ceramic spheres, the tube situated thereunder is filled at the upper and lower ends with 150 ml of ceramic spheres. 115 ml of silicon dioxide catalyst (Shell S980 G) are filled into the lower steel tube between the layers of ceramic spheres. The temperature of the upper steel tube is adjusted to 200° C., the temperature of the lower steel tube amounts to 460° C. 330 g of a 10% solution of 5-carbamoyl-4-methyl-oxazole in N-methyl-pyrrolidone are added per hour at the top of the upper tube. 100l of nitrogen gas are added hourly at the foot of the upper tube. A total of 279 g of 5-carbamoyl-4-methyloxazole in 2511 g of N-methyl-pyrrolidone are dosed in within 8.5 hours. 1828 g of pure N-methyl-pyrrolidone are removed at the head of the reactor. The reaction product is removed at the lower end of the reactor as a solution in N-methyl-pyrrolidone. The conversion amounts to >99%. In the distillative working-up of the reaction product there are obtained 592 g of N-methyl-pyrrolidone, thus a total of 2420 g (96.4%) of the N-methyl-pyrrolidone used. The amount of 5-cyano-4-methyl-oxazole obtained amounts to 222 g (93%).

EXAMPLE 4

Impure 5-carbamoyl-4-methyl-oxazole (impurities: water, ammonia, ethanol; total amount 10%) is used in place of pure 5-carbamoyl-4-methyl-oxazole.

The same reaction conditions and the same amounts of educt and solvent as in Example 3 are used. The low-boiling impurities are removed at the head of the reactor. The working-up of the reaction product is effected analogously to Example 3. The yield of 5-cyano-4-methyl-oxazole amounts to 93%.

I claim:

1. A process for producing 5-cyano-4-lower alkyl-oxazoles of the formula:

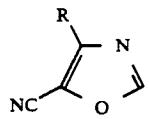

I wherein R is lower alkyl: comprising dehyrating 5-carbamoyl-4-lower alkyl-oxazole of the formula:

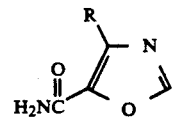

II wherein R is as above, in the presence of a silicon dioxide catalyst by forming a vapor containing said 5-carbamoyl-4-lower alkyl-oxazole and an N-lower-alkyl-pyrrolidone solvent and contacting said vapor with said silicon dioxide catalyst at a pressure of from about 50 kPa to about 300 kPa to convert said 5-carbamoyl-4-lower alkyl-oxazole to said 5-cyano-4-lower alkyl-oxazole.

2. A process of claim 1 wherein contact of vapor with catalyst is carried out at a temperature of from about 350 degrees C. to about 500 degrees C.

3. A process of claim 1, wherein R is —CH₃ or —CH₂CH₃.

4. A process of claim 1, wherein the N-lower alkyl-pyrrolidone is N-methyl-pyrrolidone or N-ethyl-pyrrolidone.

5. A process of claim 1, wherein the N-lower alkyl-pyrrolidone is diluted with water.

6. A process of claim 1, wherein the catalyst is formed silicon dioxide.

7. A process of claim 1, wherein the catalyst is silicon dioxide doped with oxides of V, Mo, Fe, Co or Zn.

8. A process of claim 7, wherein the dopant amounts to about 1–20 weight percent of the total weight of the doped catalyst.

9. A process of claim 1, wherein the catalyst has a specific surface area of about 20 m²/g to about 300 m²/g.

10. A process of claim 1, wherein said dehydration is carried out at a temperature of about 350° C. to about 500° C.

* * * * *